United States Patent [19]
Henkens et al.

[11] Patent Number: 5,217,594
[45] Date of Patent: Jun. 8, 1993

[54] CONVENIENT DETERMINATION OF TRACE LEAD IN WHOLE BLOOD AND OTHER FLUIDS

[75] Inventors: Robert W. Henkens, Durham; Junguo Zhao, Chapel Hill; John P. O'Daly, Carrboro, all of N.C.

[73] Assignee: Enzyme Technology Research Group, Inc., Durham, N.C.

[21] Appl. No.: 821,732

[22] Filed: Jan. 15, 1992

[51] Int. Cl.$^5$ .......................................... G01N 27/26
[52] U.S. Cl. .................................. 204/403; 204/412; 204/415; 204/435; 435/817; 435/288
[58] Field of Search ................ 204/403, 412, 415, 435; 435/288, 817

[56] References Cited

U.S. PATENT DOCUMENTS

| | | | |
|---|---|---|---|
| 4,581,336 | 4/1986 | Malloy et al. | 204/403 |
| 4,820,399 | 4/1989 | Senda et al. | 204/403 |
| 4,950,378 | 8/1990 | Nagata | 204/412 |
| 4,970,145 | 11/1990 | Bennett et al. | 204/403 |

OTHER PUBLICATIONS

Crumbliss, A. L., Henkens, R. W., Kitchell, B. S., Perine, S. C., Stonehuerner, J., and Tubergen, K. R., "Amperometric Glucose Sensor Fabricated from Glucose Oxidase and a Mediator Co-Immobilized on a Colloidal Gold Hydrogel Electrode," *Biosensors Technology: Fundamentals and Application*, Chapter, 13, 1990, published in USA.

Crumbliss, A. L., Henkens, R. W., Hunter, K., Kitchell, B. S., O'Daley, J. P., Stonehuerner, J., and Tubergen, K. R., "The Influence of Colloidal Gold Surfaces on Enzyme Activity," ACS North Carolina Divisional Meeting, Sep. 1988, published in USA.

Crumbliss, A. L., Henkens, R. W., Kitchell, B. S., Perine, S. C., Stonehuerner, J., and Tubergen, K. R., "Amperometric Glucose Sensor Fabricated from Glucose Oxidase and a Mediator Co-Immobilized on a Colloidal Gold Hydrogel Electrode," ACS North Carolina Divisional Meeting, University of North Carolina at Chapel Hill, Sep. 7-9, 1989, published in USA.

Crumbliss, A. L., Kitchell, B. S., Perine, S. C., Stonehuerner, J., Tubergen, K. R., Zhao, J., and Henkens, R. W., "Catalytic and Electroactivity of Irreversibly Adsorbed Enzymes at Gold Electrode Surfaces," Symposium on Protein Electrochemistry: ACS Southeast Regional Meeting (SERM), Oct. 1989, published in USA.

Crumbliss, A. L., Henkens, R. W., Kitchell, B. S., McLachlan, K. L., O'Daly, J. P., Perine, S. C., Stonehuerner, J., Tubergen, K. R., and Zhao, J., "The Use of Inorganic Materials to Control or Maintain Immobilized Enzyme Activity," Symposium on opportunities for inorganic chemistry in biotechnology, ACS National Meeting in Boston, Apr. 23, 1990, published in USA.

Henkens, R. W., Kitchell, B. S., O'Daly, J. P., Perine, S. C., and Crumbliss, A. L., "Bioactive Electrodes Using Metallo Proteins Attached to Colloidal Gold," *Recl.: Trav. Chim. Pays Bas*, 106:298, 1987.

Henkens, R. W., Zhao, J., and O'Daly, J. P., "Multi-Analyte Enzyme Electrodes for Environmental Monitoring," *Proceedings of 5th International Biotechnology Conference in Copenhagen*, Jul. 8-13, 1990.

Albery et al., "Inhibited Enzyme Electrodes. Part 3.," *Biosensors & Bioelectronics*, 5:397-413, 1990, published in Great Britain.

(List continued on next page.)

*Primary Examiner*—John Niebling
*Assistant Examiner*—Bruce F. Bell
*Attorney, Agent, or Firm*—Arnold, White & Durkee

[57] ABSTRACT

The invention relates to novel b of detecting metal ion concentrations less than about 10 μg/dl fluid. Biosensors based on the enzyme isocitrate dehydrogenase are particularly suited for detecting trace lead ion concentrations in water and in blood. Bioelectrodes are fabricated from surface deposited colloidal gold adsorbed enzyme that retains high catalytic activity Other aspects of the invention include detection devices for convenient and rapid measurement of metal ions.

30 Claims, 7 Drawing Sheets

OTHER PUBLICATIONS

Almestrand et al., "Determination of Lead in Whole Blood with a Simple Flow-Injection System and Computerized Stripping Potentiometry," *Analytica Chimica Acta*, 209:339-343, 1988, published in The Netherlands.

Baum & Czok, "Enzymatische Bestimmung vol „ ionisiertem++ Magnesium in Plasma," *Biochemische Zeitschrift*, 332:121-130, 1959.

Botré et al., "Synthesis and Inhibitory Activity on Carbonic Anhydrase of Some New Sulpiride Analogues Studied by Means of a New Method," *Journal of Medicinal Chemistry*, 29:1814-1020, 1986.

"New Rules Set for Blood Lead Levels," *Chemical and Engineering News*, p. 17, Oct. 14, 1991.

Fair & Jamieson, "Studies of Protein Adsorption on Polystyrene Latex Surfaces," *Journal of Colloid and Interface Science*, 77(2):525-534, 1980.

Guilbault et al., "Homovanillic Acid as a Fluorometric Substrate for Oxidative Enzymes," *Analytical Chemistry*, 40(1):190-196, 1969.

Guilbault, "Determination of Inhibitors," *Enzymatic Methods of Analysis*, Pergamon Press, pp. 197-209, 1970, published in Great Britain.

Holleck, "The Reduction of Chlorine on Carbon in $AlCl_3$-KCl, NaCl Melts," *Journal of the Electrochemical Society*, 119(9):1158-1161.

"U.S. CDC Releases Revised Guidelines on Childhood Lead Poisoning-Blood Lead Level of Concern Lowered to $\geq 10$ μg/dl," *ILZRO Environmental Update*, 1(10):2, 1991.

Kamata & Onoyama, "Lead-Selective Membrane Electrode Using Methylene Bis(diisobutyldithiocarbamate) Neutral Carrier," *Analytical Chemistry*, 63:1295-1298, 1991.

Kratochvil et al., "Effect of Metals on the Activation and Inhibition of Isocitric Dehydrogenase," *Analytical Chemistry*, 39(1):45-51, 1967.

Linde, "Estimation of Small Amounts of Fluoride in Body Fluids," *Analytical Chemistry*, 31(12):2092-2094, 1959.

Morrissey & Han, "The Conformation of γ-Gluobulin Adsorbed on Polystyrene Latices Determined by Quasielastic Light Scattering," *Journal of Colloid and Interface Science*, 65(3):423-431, 1978.

Sheikh & Townsend, "Aplications of Enzyme-Catalysed Reactions in Trace Analysis-VII," *Talanta*, 21:401-409, 1974, published in Great Britian.

Smit & Cass, "Cyanide Detection Using a Substrate-Regenerating, Peroxidase-Based Biosensor," *Analytical Chemistry*, 62:2429-2436, 1990.

Toren & Burger, "Trace Determination of Metal Ion Inhibitors of the Glucose-Glucose Oxidase System," *Mikrochimica Acta (Wien)*, pp. 538-545, 1968.

Tran-Minh et al., "Studies on Acetylcholine Sensor and its Analytical Application Based on the Inhibition of Cholinesterase," *Biosensors & Bioelectronics*, 5:461-471, 1990.

Smith, "Air Pollution and Forest Damage," *Chemical and Engineering News*, pp. 30-42, Nov. 11, 1991.

Trade Brochure: esa, Inc. Trace Metal Analyzer Brochure, Bedford, Mass., A, 1990.

Gunasingham et al., "Performance and Evaluation of a Handheld Electrochemical Monitor for Toxic Metals," Cole-Parmer Instrument Company, Chciago, Illinois.

CONVENIENT DETERMINATION OF TRACE LEAD IN WHOLE BLOOD AND OTHER FLUIDS

BACKGROUND OF THE INVENTION

1. Field of the Invention

The invention relates to colloidal gold adsorbed enzyme biosensors sensitive to inhibition by metal ions in fluids and in particular to bioelectrodes capable of detecting lead at concentrations at least as low as 10 $\mu$g/dl. Aspects of the invention include methods of detecting lead in various biological fluids and convenient devices incorporating the bioelectrode.

2. Description of Related Art

Certain metals have long been considered as hazardous to health or to pose an environmental threat. Some metal ions in water or other fluids are of particular interest because of toxicity to humans, cadmium, chromium, nickel, lead, thallium, zinc and arsenic being particular examples The effects of these metals may not be acute; indeed chronic toxicity is of particular concern because the metals accumulate in tissues over a period of long-term exposure. The result, especially in the very young, may be developmental abnormalities, both mental and physical.

The detrimental effects of lead in the environment have long been recognized. Lead poisoning has been detected in waterfowl due to lead shot. The elimination of tetraethyl lead as an octane booster in gasoline was part of an effort to prevent this metal from further contamination of soil and water supplies. However, the use of lead in glazes, paints and coatings, to mention a few examples, has occurred over long periods of time; in fact, lead in pottery may have contributed to the demise of earlier civilizations As a result of long-term use of lead in the past in so wide a range of products, it is difficult to avoid exposure to this element Lead solder joints in water pipes, for example, contribute to the lead content of drinking water. Modern interior paints are lead-free, but in older homes there may be significant exposure to lead in the surroundings from older lead-based paints, even when such paint layers are coated with the newer lead-free paints. Unfortunately, this has created a real risk of lead toxicity for those groups most susceptible; children.

The long term effect of lead on the health of children exposed to unacceptable levels is calculated to be very significant. This will ultimately reflect in higher health costs, due to increased disability and treatment required. This is of concern to health care professionals and to the federal government, to the extent that new rules related to a "threshold of concern" have been provided in guidelines set by Health & Human Services' Centers for Disease Control (C&E News, 1991). It is hoped that programs being developed to detect the presence of lead in groups at risk for the most damage from lead poisoning will lead to rapid, reliable methods of detecting low levels of lead in individuals. Unfortunately, it is difficult at best to detect lead in body fluids such as blood and it would be impractical to take tissue samples, for example brain tissue samples, to determine lead concentrations.

A simple, reliable method of detecting levels of lead in blood is not available. Current technology relies on time-consuming methods such as computerized stripping potentiometry (Almestrand, et al., 1988). Although the instrumentation required for this determination is not unduly complex, highly skilled technicians are needed. This is also true for a commercially available hand held monitor, ElectraScan EC-1Pb monitor for lead detection, from Eutech cybernetics, Singapore (Gunasingham, et al., 1989).

Routine analysis of metals has generally relied on atomic absorption spectrometry. However, the equipment required for analysis is expensive. Moreover, the method exhibits lower accuracy and sensitivity toward lead as compared to anodic stripping voltammetry Instruments currently available for monitoring trace metals generally require highly trained personnel to perform relatively sophisticated techniques. Consequently, analyses are performed in centralized laboratories set up for routine multiple sample analysis. However, there is no instrumentation available for use in the field or in the physician's office allowing rapid metal determinations with simple portable instruments that do not require highly technically trained personnel.

Trace metal determination based on metal-enzyme interaction has taken advantage of either activation or inhibition of an enzyme by a metal, usually specific for the enzyme. Fluoride has been measured by its inhibition of liver esterase catalysis of a butyrate substrate (Linde, 1959) and magnesium has been measured in plasma by isocitric dehydrogenase activation (Baum and Czok, 1959). Titration determinations or rates of TPNH formation measured spectrophotometrically have been reported to be useful for measuring levels of activating metals such as manganese, magnesium and cobalt. Inhibiting metals such as lead can also be measured (Kratochvil, et al., 1967).

Analysis of trace metals based on inhibition of an enzyme's ability to produce hydrogen peroxide and oxidize homovanillic acid to a fluorescent product has also been explored Horse radish peroxidase inhibition was linear over a range of 10–185 $\mu$g/ml of lead (Guilbault, et al., 1968). Metal ion inhibition of the enzyme glucose oxidase with mercury (II), Ag(I) and Pb(II) has suggested that these metals are detectable at low levels although strong buffer-interactions were obtained when lead was present, casting doubt on the viability of the method generally to measure lead in trace amounts (Toren and Burger, 1968).

Of a few reported enzyme-inhibitor electrodes, most use $CO_2$ and pH electrodes (Tran-Minh et al., 1990; Botre et al., 1983) which have a small, nonlinear response. Most potentiometric sensors detect the enzymatic reaction product, not the enzyme activity directly. The response time to inhibitors is usually long because the inhibition effect can show up only after the product has diffused away from the electrode surface. When a pH electrode is used, the signal largely depends on the pH and the buffer capacity of the sample solution.

Amperometric enzyme-inhibitor electrodes have been reported, either with rather classical configurations in which the enzyme and promoter solution are fixed on or near the electrode surface with a dialysis membrane (Albery et al., 1990) or with covalently bound enzymes and complicated electrochemical techniques with soluble electron transfer mediator in the sample solution (Smit and Cass, 1990). All the reported inhibitor sensors use wet enzymes, either on a membrane or electrode surface, or between a membrane and an electrode surface (or wet mediator in amperometric sensors). This makes it difficult for long-term storage.

Moreover, none is reported to work with microcells using simple electrochemical techniques.

SUMMARY OF THE INVENTION

The present invention addresses one or more of the foregoing problems in providing a simple, reliable method of detecting metals in fluids, particularly the detection of trace amounts of toxic metals such as lead and mercury as well as other metals. The method is based on a novel bioelectrode employing colloidal gold adsorbed enzymes that are inhibited, often irreversibly and frequently at submicromolar concentrations of metal ion. Biosensors constructed from such novel bioelectrodes may operate with or without a mediator. Reduction of oxidation current in the presence of an oxidizable substrate and an enzyme cofactor is detectable without a mediator and directly related to the amount of metal ion present, as in the detection of lead using an isocitrate dehydrogenase electrode. The invention also includes bioelectrodes suitable for incorporating into lead detection devices.

One aspect of the invention includes a biosensor sensitive to trace levels of metal ions. Such biosensors include a reference electrode, a counter electrode and a working electrode, or optionally, a counter electrode combined with the reference electrode. An enzyme is located on or near the surface of the working electrode. In the presence of a suitable substrate the enzyme will catalyze a redox reaction. A current generated by the redox reaction will be adversely affected by selected metal ions, and in some preferred embodiments, at concentrations less than about 10 $\mu$g/dl.

Biosensors of the invention may be used to detect a wide variety of nontoxic and toxic metal ions including mercury, cadmium, silver, zinc, copper, calcium, manganese, thallium, lead and the like. Sensitivity and selectivity of the biosensor will depend on the enzyme selected. In order to be effectively inhibited by low metal ion concentrations, it is preferable that the enzyme, or enzymes, selected is strongly and irreversibly inhibited by the metal ion. In most situations, inhibition is preferable in the micromolar or even lower range. In a most preferred embodiment, colloidal gold immobilized isocitrate dehydrogenase may be used to detect submicromolar to nanomolar concentrations of lead ion. Yet another embodiment is a colloidal gold adsorbed alcohol dehydrogenase sensitive to low concentrations of mercury ion.

It should be recognized that enzyme inhibition constants of enzymes selected for particular use biosensors may differ depending the physical state of the enzyme. Constants may be quite different for immobilized species compared with the same species in solution. While solution inhibition constants in the nanomolar range may suggest suitability of an enzyme as a detection agent for low levels of inhibition, the constant may change after immobilization, thus requiring some degree of experimentation after potentially suitably enzymes have been selected on the basis of solution inhibition constants.

In a novel aspect of the invention, a colloidal gold adsorbed enzyme selected for detection of a desired metal ion is deposited at or near the surface of a working electrode portion of the biosensor. High activity of an enzyme is retained when it is first absorbed onto colloidal gold particles and then deposited onto the surface of a working electrode. Suitably sized colloidal gold particles for absorption are generally in the range of 25 to 100 nanometers, with 30 nanometers being a preferred range for absorption. While the invention has been demonstrated using colloidal gold particles for absorption, other colloidal conducting particles are contemplated as useful. For example, colloidal carbon, colloidal palladium, colloidal platinum and the like. Selection of the appropriate material and particle size may be optimized for the enzyme selected; however, compatibility of the metal particles with the working electrode surface material and conductivity and electron transport properties, should be taken into account in each case.

Enzymes adsorbed onto colloidal gold particles may be deposited on a working electrode surface by any of several methods, including spray deposition, evaporative deposition, and electrolytic deposition. In many cases, any of these techniques is equally effective in providing a useful biosensor; however, in terms of cost, speed and preparation with a view to field use, evaporative deposition is preferred, and is particularly preferred in the preparation of immobilized colloidal gold adsorbed ADH and ICD. Evaporative deposition is simply a matter of allowing an enzyme colloidal gold solution to dry at room temperature or below on the surface of the working electrode.

A surprising aspect in the construction of enzyme-colloidal gold biosensors that detect analytes by inhibition of an oxidation current is the effect of the amount of enzyme on ability to detect analyte. When it is desirable to detect relatively low amounts of analyte, relatively small amounts of the sensing enzyme should be deposited on the electrode surface. On the other hand, larger amounts of deposited enzyme will not detect trace levels of metal ion inhibitor, but are quite adequate for determination of micromolar amounts of metal ion inhibitors.

Enzymes useful in the practice of the present invention include those capable of catalyzing redox reactions. Cofactors typically associated with such enzymes include NADP and AND. During the oxidative reaction catalyzed by such enzymes, NADP or AND is reduced to NADPH or NADH respectively during the process. Oxidation currents have been detected without added mediators; however, mediators may be desired to enhance efficiency. Suitable mediators include ferrocene and its derivatives, ferricyanide, N-methylphenazine methosulfate and related compounds such as N-ethyl phenazinium and phenoxazine and the like. Generally, mediators will be selected based on the electrochemical properties of the bioelectrode depending on the enzyme and substrates chosen. Mediators should be in their oxidized forms initially to reduce background signal.

Another aspect of the invention includes a working electrode surface-coated with a membranous or gelatinous film containing a redox enzyme. The redox enzyme will typically be dispersed within the gelatin or membrane material and then applied to the surface of the working electrode. Enzyme cofactors such as NADP or AND may also be included in the gelatinous film with the enzyme. Alternatively, such cofactors may be present in the bulk solution where they may freely enter and exit the membrane material with access to the electrode surface and to the gelatinous film immobilized enzyme. Suitable film materials will include substances that are compatible with the enzyme selected. For example, any of a variety of carrageenans, such as k-carrageenan, hydrophilic polymers or hydrophilic gels such as agar. It is also contemplated that colloidal gold itself may be provided as a semi-permeable film over a deposited colloidal gold enzyme surface. Colloidal gold films are porous, may have various charges on surfaces and are recognized as binding readily with a wide range of organic species, including proteins. A negatively charged colloidal gold film, readily prepared from the colloidal gold solutions herein described, is expected to exhibit cation selectivity, for example, lead, mercury, cadmium, etc. Relatively large negatively charged species such as some polymers and large complexes would tend to be excluded while inorganic anions such as sulfate or chloride would likely remain unaffected or only weakly excluded. Before incorporation into the film, an enzyme is preferably adsorbed onto colloidal gold particles.

The working electrode surface of the biosensor of the present invention is typically a conducting material such as gold, platinum, or carbon. A most preferred surface is glassy carbon.

Biosensors of the present invention may optionally include both a cofactor such as NADP or AND and a mediator. Mediators may be associated with the enzyme through hydrophobic association, ionic interactions or by covalent bonding. Alternatively, mediators or cofactors may also be included within a film used to immobilize selected enzymes near the working electrode surface. It is also possible to coat a mediator on the electrode surface, e.g., an insoluble compound on a surface will slowly dissolve to provide a relatively low but constant amount of mediator or cofactor.

One aspect of the present invention is a bioelectrode surface modified with an enzyme capable of catalyzing a redox reaction in which a detectable current is generated. Such electrodes include colloidal gold adsorbed enzyme deposited on a conducting surface of the bioelectrode. In a particular embodiment, an enzyme sensitive to inhibition by trace lead levels, preferably isocitrate dehydrogenase, is inhibited in the presence of lead ion concentrations less than about 10 $\mu$g/dl. Current from oxidation of a substrate, preferably isocitrate, is detectably affected and may be measured when the bioelectrode is coupled with a reference electrode and the proper detection systems. A typical bioelectrode useful for the detection of trace levels of lead is based on immobilized isocitrate dehydrogenase.

Another aspect of the invention is a method of detecting lead ion in fluids. A sample suspected of containing lead ion is contacted with the working electrode surface of the herein described bioelectrode. An enzyme substrate is added to the sample typically isocitrate. In the presence of trace lead metal ion concentrations there will be a decrease in generated currents, compared with current generated in the total absence of lead ion. The current decrease may be correlated with lead ion concentrations, particularly below 10 $\mu$g/dl.

The disclosed method is suitable for determining trace metal ion concentrations in water, waste water, biological fluids such as urine, saliva, sweat, tissue exudate and the like. The method may also be used for detecting trace lead ion concentrations in whole blood.

The present invention has been demonstrated with aqueous samples; however, an important contemplated use is direct detection of metal ion levels in solid materials such as paint. Detection involves in principle the same basic bioelectrode herein disclosed Biosensors may be designed to transfer, through a semipermeable film for example, trace amounts of metal from a surface to a suitable bioelectrode sensor that is detectably inhibited by such low metal concentrations.

The biosensors of the present invention are useful in fabricating an apparatus for detecting lead ion levels in fluids. Such an apparatus will have a receptacle for containing a fluid sample. Suitable receptacles might include any sort of a container such as a test tube, glass vial which has a suitable and convenient shape The receptacle should be made of materials that will not contaminate the sample with lead. The biosensor in the apparatus will be placed to allow contact of the biosensor with the fluid sample in the receptacle and a detector positioned to receive a signal from the biosensor. The signal obtained from the biosensor will arise from a current generated from a redox reaction catalyzed by the enzyme which is located on the biosensor working electrode surface. For the detection of lead ions, the enzyme is most preferably isocitrate dehydrogenase. A typical redox reaction catalyzed by isocitrate dehydrogenase will include isocitrate as a substrate when using isocitrate dehydrogenase as the biosensor system. Current generated by a redox reaction is typically inversely related to an amount of lead present in the fluid sample. The disclosed apparatus may further include a counter electrode and electronic analysis and display components. For particular applications, the electronic analysis and display component may be reusable while the bioelectrode may be disposable.

DETAILED DESCRIPTION OF THE PREFERRED EMBODIMENTS

Figure 2:
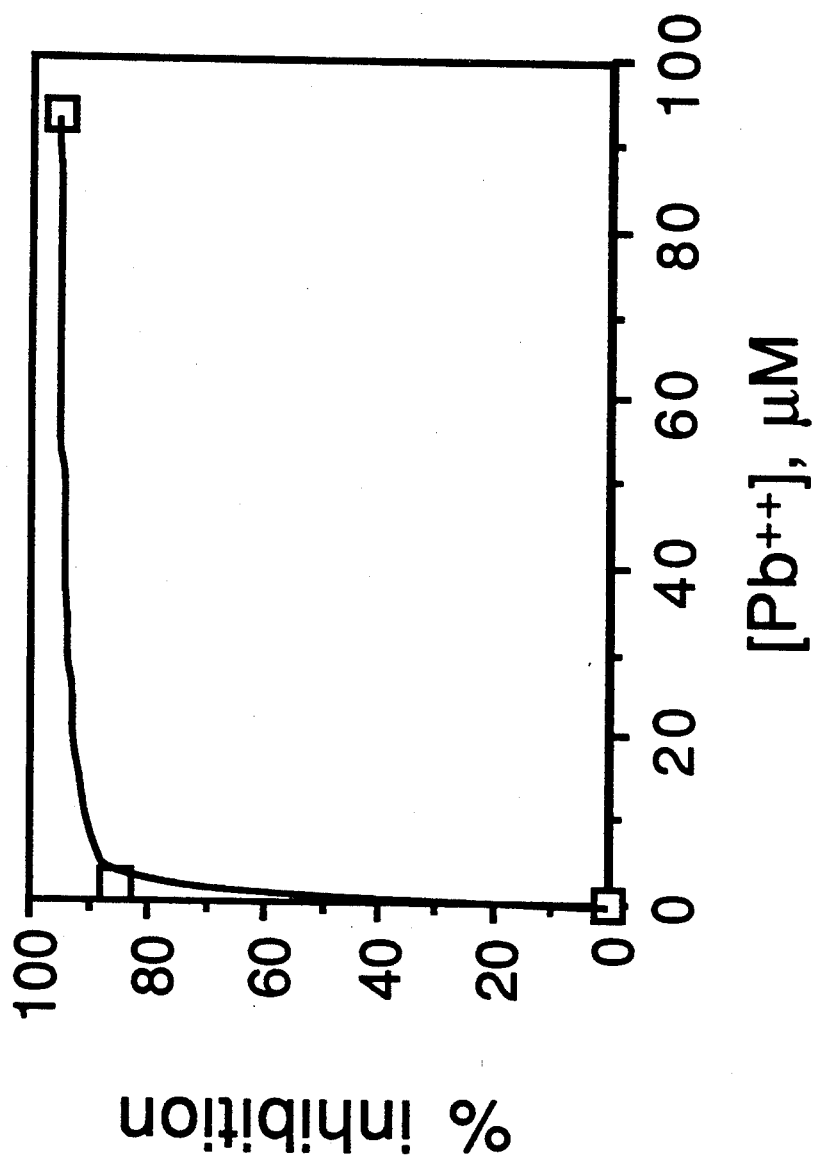
FIG. 2 shows the amperometric response to lead ion using a colloidal gold/ICD bioelectrode prepared by deposition on glassy carbon.
Figure 3:
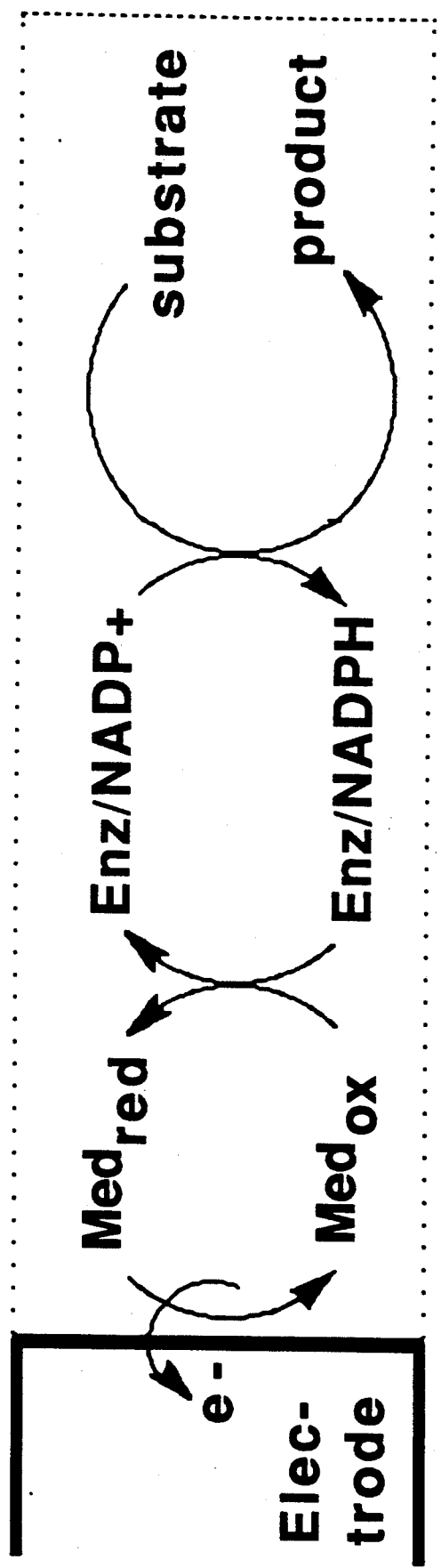
FIG. 3 is a diagram showing the general operating principle of a bioelectrode.

The present invention relates to novel bioelectrodes capable of responding to metal ions, and is particularly concerned with colloidal gold adsorbed enzymes immobilized on suitable substrates. Electrodes prepared from enzymes sensitive to low metal levels, particularly isocitrate dehydrogenase and alcohol dehydrogenase which are selectively inhibited by lead and mercury respectively, generate detectable oxidation currents that show a linear decrease in current in the presence of increasing levels of metals to which they are sensitive. The general oxidation/reduction scheme is shown in FIG. 2.

The reactions involved in using a particular enzyme, isocitrate dehydrogenase, are shown. A typical mediator is N-methylphenazine methosulfate which operates at 0 V relative to the Ag/AgCl couple.

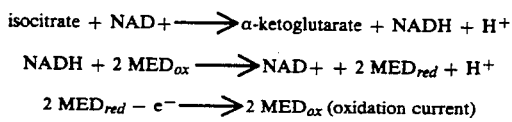

$$\text{isocitrate} + \text{NAD}+ \longrightarrow \alpha\text{-ketoglutarate} + \text{NADH} + \text{H}^+$$
$$\text{NADH} + 2\,\text{MED}_{ox} \longrightarrow \text{NAD}+ + 2\,\text{MED}_{red} + \text{H}^+$$
$$2\,\text{MED}_{red} - e^- \longrightarrow 2\,\text{MED}_{ox}\ (\text{oxidation current})$$

Current may be detected directly at the electrode surface during oxidation of the cofactor, either directly or through a mediator.

Pig heart NADP-linked isocitric dehydrogenase (ICD, EC 1.1.1.42), an oxidoreductase, is sensitive to trace level of lead ion as low as 1 $\mu$g/dl. Like many enzymes, ICD is inactive or only slightly active unless $Mg^{++}$ or $Mn^{++}$ is present. In fact, at low concentrations of activator, e.g., <200 ppb $Mn^{++}$, the activity of ICD is proportional to $Mn^{++}$ and may be used to determine activator concentration (Guilbault, 1970). Inactivation by inhibitors may also be used to determine inhibitor concentration. Specificity of enzymes for activators, or inhibitors, is not as great as for the natural substrate of the enzyme, but in some cases inhibitor concentration may be selectively determined. Silver and mercury have been determined in the presence of each other using isocitrate dehydrogenase (Mealor and Townshend, 1968). However, until now, there has been no satisfactory rapid amperometric method to determine of lead ion based on ICD inhibition, much less a simple method to determine low lead ion concentrations in whole blood.

As used herein, a bioelectrode refers to a single electrode, the working electrode, at the surface of which an electron transfer takes place representing a reaction catalyzed by an enzyme located on or near the surface of the electrode. Such a bioelectrode when set up with an appropriate reference/counter electrode may constitute a biosensor. Within the meaning of the present invention, a biosensor is intended to indicate a system capable of producing a signal that may be related to a reaction catalyzed by an enzyme constituting the biosensor. Biosensors comprising bioelectrodes will operate by producing a current related to the activity of an enzyme catalyzing electron transfer.

Enzymes have been immobilized at surfaces, but a major problem has been to maintain catalytic activity of enzymes immobilized on surfaces. This is of particular concern when ability to transfer electrons is involved, as with redox enzymes and such species as oxidases and reductases. The present invention takes advantage of the ability of colloidal gold adsorbed enzymes to retain high activity. Additionally, the deposition of colloidal gold adsorbed enzyme onto a working electrode surface has provided a catalytically active enzyme from which a detectable current can be generated.

A colloidal gold surface is distinctly different from flat bulk gold. Although the exact nature of the colloidal gold/protein/electrode surface interaction is not completely understood, there are several properties of colloidal gold that may enhance electron transfer between a redox protein and an electrode surface. Colloidal gold particles have high surface to volume ratio with high surface energy. Uncontaminated gold sol surfaces are highly active and can interact strongly with protein molecules. Smaller colloidal gold particles, in the range of 30 nm, provide an adsorbed protein molecule some freedom in orientation thereby increasing the possibility that a prosthetic group, or cofactor, is closer to the metal particle surface. This makes the distance for electron transfer between the protein and the metal particles shorter, and therefore charge transfer is easier. With ICD/gold sol deposited on an electrode surface, colloidal gold particles covered with ICD are able to function as electron-conducting pathways between the prosthetic groups and the electrode surface to facilitate the electron transfer process.

The larger effective surface area appears to allow more enzyme molecules to be immobilized at or near the electrode surface. The possibility for multilayers of effective Au-enzyme layers may be another mechanism by which the signal from colloidal gold assisted immobilization is increased.

Assuming that the average diameter of the sol particle is 30 nm and the density is 17.0 g/mL, then 3 $\mu$l of 7.5 mg Au/mL sol deposited onto a glass carbon surface of 3 mm in diameter is equivalent to about 12 layers of Au sol particles. In the case of HRP-Au sol this surface coverage gives the best performance, both with and without a mediator. Addition of more Au layers causes the unmediated response to deteriorate slightly but does not much affect the mediated response, suggesting that the deposited Au layers are not very porous and that the accessible depth is no more than 12 layers of deposited Au sol. Even within the 12 layers, only the outermost layers are of importance, because changing from 4 to 12 layers increased the signal by only 10–20% with or without a mediator. This suggests that only a few layers of the deposited Au-enzyme are porous. In consideration of both the electrode performance and cost, 3 $\mu$l ICD-Au sol appears to be optimum for a 3 mm diameter glassy carbon surface.

Although apparently only the outermost gold layers contribute the major portion of accessible enzyme molecules, enzyme loading and mediator effects with colloidal gold assisted immobilization are still much higher when compared with simple adsorption on flat surfaces. Spectroscopic data for the enzymatic activity of some enzymes adsorbed on colloidal gold before deposition on the electrode surface indicate that the active enzyme coverage on the gold sol particle surfaces is only about 40% of a theoretical compact monolayer. This is consistent with the data obtained by other workers for adsorption of $\gamma$-globulin onto latex particles (Morrissey and Han, 1976; Fair and Jamieson, 1980). The likelihood of multilayer adsorption of protein molecules on a solid support surface is thought negligible. If the adsorption is not specific, the protein molecules can have multiple orientations on the surface. The strong interactions between the protein and the Au sol surface may increase the surface density of the adsorbed protein, and some of the restricted orientations may also favor the direct electron transfer between the protein molecules and the conductor surface. It is likely that all of the enzyme molecules are on the first layer of the adsorbed surface, but only part of the molecules have the correct orientation for direct electron transfer.

The electrode surface on which an enzyme/colloidal gold sol is deposited may be any appropriate conducting surface such as gold, platinum, glassy carbon and the like. In preparing lead sensitive electrodes with isocitric dehydrogenase, a glassy carbon surface is preferred.

Deposition of a lead-detecting enzyme on or near an electrode surface may be accomplished in several ways, including electrodeposition, evaporation, spray deposition (e.g., aerosol), or electrolyte deposition. Electrodeposition may be accomplished by setting a working electrode at an appropriate potential, for example 1.6 v vs. a Ag/AgCl reference electrode with a platinum wire counter electrode. Using a two electrode system with a glassy carbon disk electrode held at a fixed position in a cavity in a lucite block, or other suitable material, a platinum plate at the bottom of the cavity serves as a reference/counter electrode. Electrodeposition may be performed at constant current or constant potential and optimized for the enzyme to be deposited.

Electrolyte deposition is a method whereby an enzyme/Au sol is applied to the surface of an electrode such as glassy carbon followed by an equal volume of an electrolyte such as $CaCl_2$. The latter solution causes the sol to precipitate and after a period of time at ambient temperature the electrode may be rinsed and stored in buffer at 4° C.

Solvent evaporation is preferred for ease and convenience. The method is simply performed by applying a fixed amount of Au-enzyme sol to the electrode surface and then drying at room temperature or near 4° C.

Methods

A Pine Instrument dual potentiostat interfaced to an IBM-386 computer was for enzyme electrode measurement. The system is controlled with an ASYST program (J. Zhao, Enzyme Technology Research Group, Inc., 710 West Main Street, Durham, NC 27701).

Cyclic voltammetry measurements were used to determine amounts of immobilized mediator Cyclic voltammograms were obtained in the quiescent state. In steady state amperometry experiments the potential was set at 0 V/Ag in stirred buffer with regular sized cell or in quiescent solution with a micro cell and the steady state current was measured. A fixed potential method or chronoamperometric method was used to determine enzyme inhibition.

In the chronoammetry method, the working electrode was held at a fixed potential while current versus time data were collected with the aid of a computer until steady state was reached. This was observed either from a real-time graphic display and/or the numeric display on the computer screen. After measurement was complete, the computer was set to automatically provide a calibration curve of percentage inhibition vs. inhibitor concentration, heterogeneous binding constants for reversible inhibitors, and/or binding rate constants for irreversible inhibitors. Programs were modified as required.

In general, enzymes were purchased as indicated and used directly. Results were improved in some cases after the stock enzyme was purified by dialysis. Isocitrate dehydrogenase (Sigma, St. Louis, MO, ICD Type VI) was dialyzed against buffer containing buffer and manganese ion. If extensive dialysis was performed, substantial enzyme activity was lost; therefore, manganese ion was added to the dialysis buffer.

The following examples are intended to illustrate the practice of the present invention and are not intended to be limiting. Although the invention is demonstrated with isocitrate dehydrogenase and alcohol dehydrogenase, numerous variations of these enzymes are contemplated without changing the enzyme's susceptibility to irreversible inhibition by low metal concentrations. Likewise, other enzymes with different substrate specificity but similar selective sensitivity will also be appropriate.

EXAMPLE 1

The following example illustrates the detection of trace amounts of lead ion in aqueous medium through the inhibition of ICD in homogeneous solution.

Dialysis of ICD and Selection of Buffer

Commercially available ICD (Sigma Chemical Company, St. Louis, MO) typically contains considerable amounts of sulfate or EDTA that interfere with lead ion inhibition of ICD. Dialysis of ICD against low ionic strength phosphate buffer lost most of its activity which was restored by addition of $Mn^{++}$. Dialysis against Tris buffer containing a low concentration of Mn did not affect ICD activity.

Buffer selection was important because of potential interactions of the buffer with lead ion. Tris buffer did not cause interference, while carbonate or phosphate buffers were unsatisfactory because of lead ion interactions.

Mediator

NADPH was directly oxidized at high potentials (>0.7V vs. Ag/AgCl) on carbon electrode. However, at this high potential the background current was high. Additionally, the electrode surface was fouled, presumably due to polymerization during the oxidation process. Direct oxidation of NADPH produced a background current of approximately 900 nA while the total current with isocitrate was only about 1600 nA.

Ferricyanide produced a relatively high background signal because of operation at potentials >0.2V vs. Ag/AgCl. N-methylphenazine methosulfate produced a background signal of about 20 nA without isocitrate while the total signal with isocitrate was more than 500 nA at 0 V vs. Ag/AgCl.

Microcell

Figure 1:
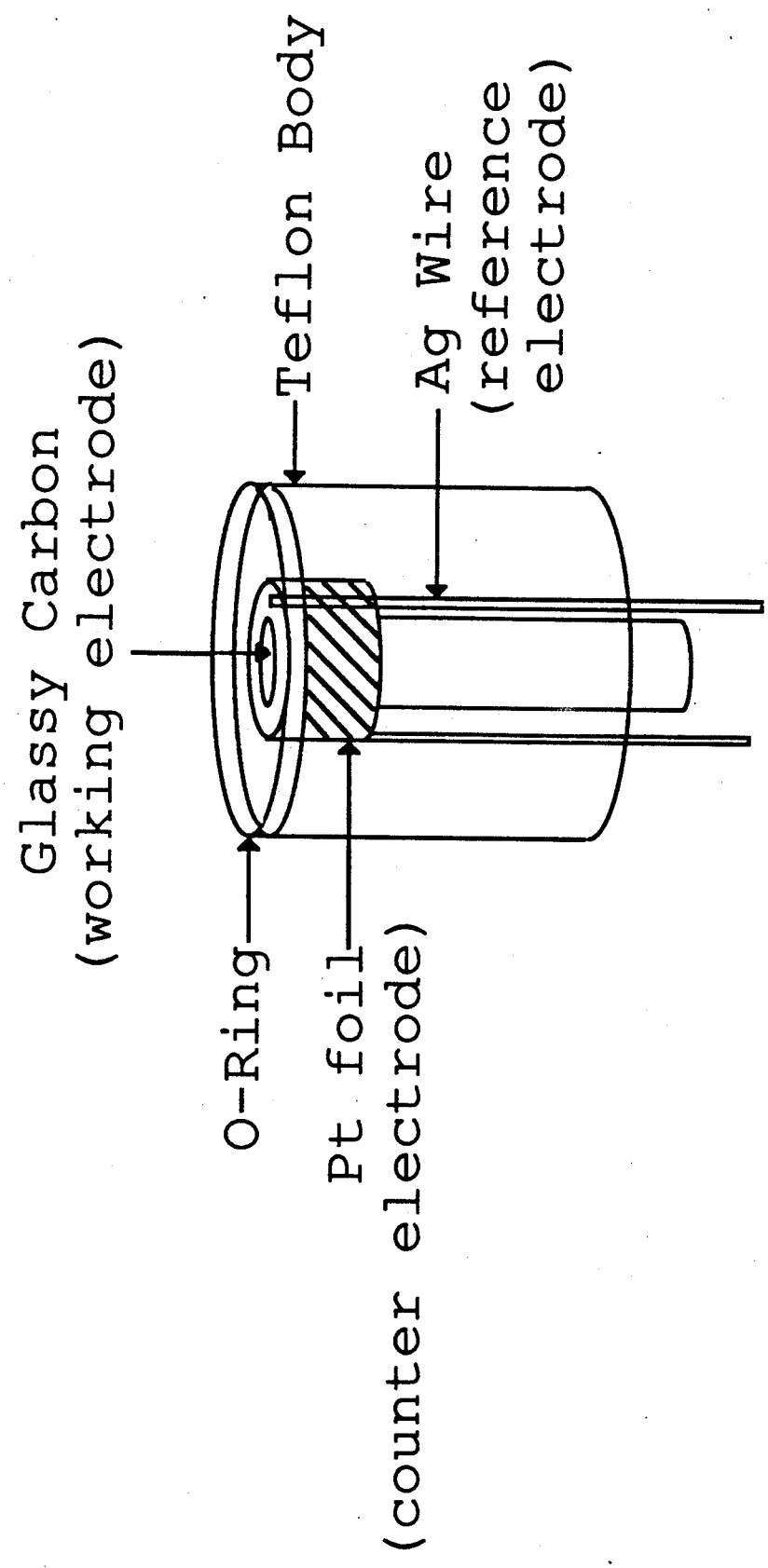
FIG. 1 illustrates a coplanar carbon electrode consisting of a planar three-electrode cell with a sample capacity of about 200 $\mu$l.

A glassy carbon rod of 3 mm diameter was wrapped in teflon tubing as working electrode and surrounded with a layer of Pt foil as the counter electrode with a silver wire placed in between as the reference electrode. At least one layer of teflon was inserted between two of the three electrodes. All three electrode surfaces were on the same plane. Tubing was fixed on the top of the coplanar electrode surface with an O-ring, forming a microcell of 100–200 µl in volume. Microcell configuration is shown in FIG. 1.

Measurement of Lead in Aqueous Solution

To the microcell was added in sequence: 100 µl 50 mM pH 8.5 Tris buffer, ca. 0.3–0.4 units ICD and, after 15 min, 5 µl 25 mM NMP-MS, 5 µl 60 mM NADP. The background current was measured at 0 V. 10 µl of 0.5 M isocitrate was added and the current measured again. The difference in the two signals was taken as due to the oxidation of isocitrate catalyzed by ICD.

To measure lead inhibition of ICD, lead ion was added to the above solution after addition of ICD but 15 min prior to the addition of NMP-MS and NADP. The current difference with isocitrate was due to inhibition of ICD by the added lead. Typical data are shown in Table 1. FIG. 2 indicates the sensitivity of the electrode to lead ion concentrations in the submicromolar range.

TABLE 1

| $[Pb^{++}]/\mu M$ | 0 | 1.89 | 90.9 |
| --- | --- | --- | --- |

| TABLE 1-continued | | | |
|---|---|---|---|
| current/nA | 1480 | 218 | 26 |
| % inhibition | 0 | 85.3 | 98.2 |

$K_i$=0.33 μM or 6.83 μg/dl lead

The presence of the mediator NMP-MS interfered with inhibition of the enzyme by added lead ion. The methosulfate group apparently caused the lead to precipitate.

EXAMPLE 2

The following example illustrates a typical preparation of an active enzyme adsorbed to colloidal gold. Such enzymes may be used to prepare bioelectrodes, generally by evaporative or electrodeposition of the enzyme/colloidal gold solution onto a suitable electrode surface.

Colloidal Gold Adsorbed ICD

Colloidal gold solutions were prepared by adding a solution of 1% aqueous sodium citrate to a boiling rapidly stirred solution of gold trichloride and refluxing for 30 min. Final concentrations (w/w) were 0.01% HAuCl4 and 0.03% sodium citrate The particle size was estimated by filtration of the sol through polycarbonate membranes (Nuclepore Corporation, Pleasanton, CA) of varying pore size using an Amicon micro ultrafiltration unit Approximately 40% of the sol passed through a 500 A Nucleopore filter and was quantitatively collected on a 300 A Nucleopore filter.

The gold sol was concentrated by centrifugation at room temperature. The concentrated sol was mixed with appropriate amounts of dialyzed isocitrate dehydrogenase solutions Then a fixed amount of the Au-ICD sol was evaporated on a coplanar carbon electrode surface and the activity measured The ICD concentration profile in the Au-ICD sol was constructed vs. the measured immobilized activity to determine the optimum composition of the Au-ICD sol.

At low ICD loadings, the enzyme activity was too low to generate a detectable signal. As the loading increased the ICD-Au sol became unstable and precipitated At higher loadings the sol became stable and the immobilized ICD activity was good.

Electrochemical Measurement of Immobilized ICD Activity

After evaporation of ICD-Au sol onto a carbon electrode surface, the electrode surface exhibited a yellow-gold appearance which was not washed off. The electrode surface was briefly rinsed with water to remove any loosely bound material before measurements were made. Buffer solution with NMP-MS and NADP was added to the microcell. Background current was measured, then isocitrate added and current again measured Typical background and sample signals were 25 and 550 nA respectively.

The basic operational principle for ICD is shown in FIG. 2. An electron transfer mediator for efficient charge coupling with the electrode surface is required. When substrate concentration is sufficiently high, the generated oxidation current signals are directly proportional to the total amount of enzyme immobilized on the electrode surface. A mediator carries electrons between the enzyme(cofactor) and the electrode surface. Substrate is consumed with the production of a catalytic current.

EXAMPLE 3

The following example illustrates several methods contemplated for the detection of lead in whole blood using the bioelectrode of example 2. The addition of whole blood to the microcell of example 2, regardless of lead content, reduced current signal.

A bare coplanar carbon electrode was used to determine whether a current could be generated. In a microcell containing 0.1 ml Tris buffer with appropriate amounts of ICD, NMP-MS, NADP and isocitrate (see Example 1) the electrode produced an oxidation current at 0 V relative to Ag/AgCl.

Whole blood interfered with the electrode response to lead in a solution where ICD, NADP, NMP-MS, isocitrate, blood and buffer are mixed together. Presence of the blood increased the viscosity of the mixture and slows the diffusion process of molecules such as NADP (mw ca. 743) and NMP-MS which are fairly large and have only limited concentrations in practical usage. Several methods are envisioned to overcome this problem, including:

Co-immobilization of Key Elements

The interference arises from the low usable concentrations of ICD, NADP and NMP-MS. When diffusion processes are slow because of solution viscosity, the generated electric signal is reduced. If all key elements required for signal generation are immobilized on or near the electrode surface, long range diffusion or mass transfer is no longer necessary for signal generation and interference is eliminated.

Alternatively, a mediator in the form of an insoluble conducting salt NMP-TCNQ, NADP and ICD are co-immobilized at the electrode surface. Only enzyme substrate, isocitrate, is then required for signal generation and this is added in excess to overcome diffusion limitation.

Co-immobilization of ICD, NADP and an insoluble mediator is feasible and practical. It is contemplated that blood interference will be greatly reduced or eliminated

Two-Step Method

Lead inhibition and signal measurement will be separately performed. The bioelectrode is first treated with a blood sample containing lead for a fixed amount of time during which lead ion will inactivate the enzyme. The blood is rinsed off and signal measurement quickly determined Rinsing will remove the blood and reduce blood interference without altering lead ion inhibition. The two-step method will eliminate any blood interference and will remove any potentially interfering species in the blood sample that are electrochemically active.

Alternatively, the blood sample is treated before measurement. Several appropriate methods of treatment are contemplated.

Dilution of Sample

The blood sample will be diluted with a buffer containing a detergent such as SDS to hemolyze the blood, or, treated with a lead complexing agent. Appropriate dilution of the sample will reduce blood interference to a tolerable level and may facilitate the inhibition process.

Solvent Extraction

Lead in blood will be extracted into an organic solvent, in a manner analogous to that routinely used in the atomic absorption method of lead determination. Once extracted into an organic phase, inhibition is performed directly in the organic solvent, provided that the solvent selected is one in which the immobilized enzyme is stable. Alternatively, the enzyme electrode is treated so that there is a stationary aqueous layer on the electrode surface allowing lead to partition from the organic phase to the thin aqueous layer where it will inhibit the immobilized enzyme. The electrode surface is coated with a thin hydrogel layer above the immobilized enzyme, the gel being wetted prior to application of the organic solvent into which the lead ion has been extracted.

Yet another option is to extract the organic phase containing the lead into the aqueous phase prior to inhibition measurements.

Lead-ion Selective Membrane

Figure 4:
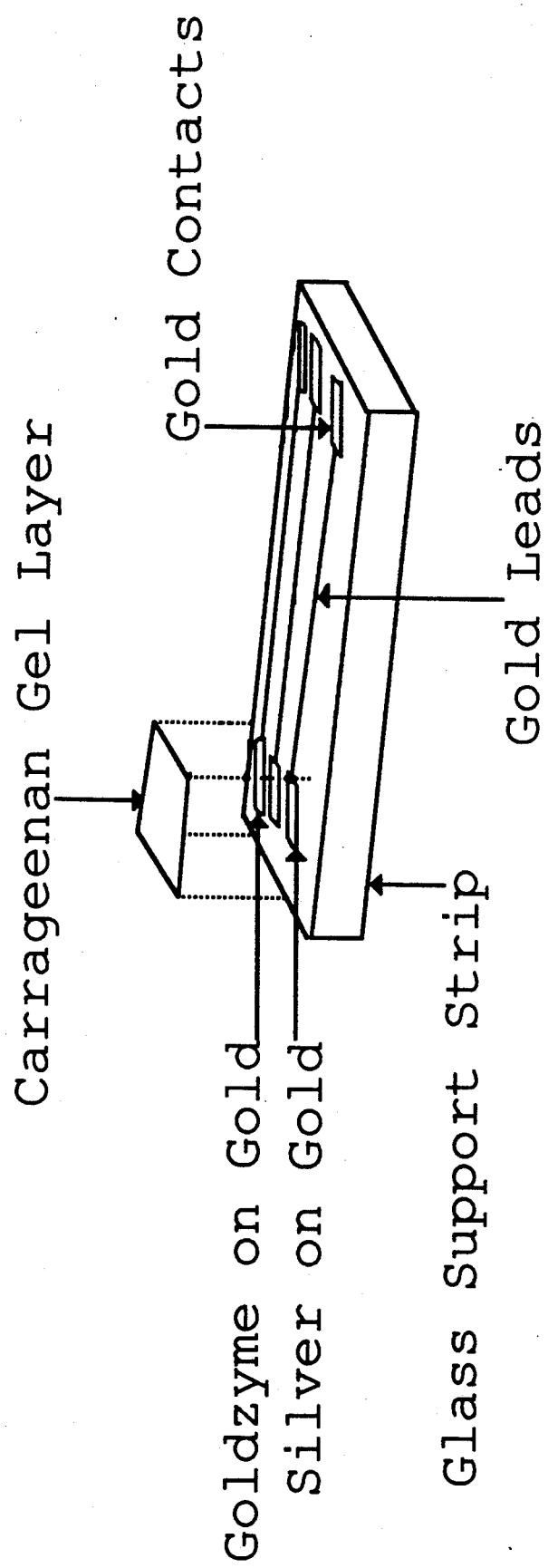
FIG. 4 schematically represents a portable sensor tip.

Lead selective ionophore-doped PVC membranes have been studied by others and shown to operate in the sub$\mu$molar range (Kamata and Onoyama, 1991). The combination of the disclosed bioelectrode and a lead-sensitive membrane will increase total selectivity and sensitivity (FIG. 4).

EXAMPLE 4

Modification of colloidal gold immobilized ICD with glutaraldehyde was attempted. Glutaraldehyde inactivated the enzyme.

Glutaraldehyde was added to ICD-Au sol either before deposition or after deposition on the electrode surface but before the surface became dry. The final glutaraldehyde concentration in the sol was between 0.1 to 0.3% by volume. The presence of glutaraldehyde did not produce a stronger or better enzyme-Au coating.

EXAMPLE 5

The following example demonstrates that an organic conductor modified electrode is effective without further added soluble mediator.

Li-TCNQ 10 g Sigma (St. Louis, MO) TCNQ was dissolved in 1000 ml boiling acetonitrile, then 20 g LiI in 100 ml boiling acetonitrile was added. Purple precipitate was formed. The mixture was left at room temperature for 2.5 hr and then filtered, washed with acetonitrile until the washing was bright green. The purple solid was air-dried overnight.

NMP-TCNO 6.8 g Li-TCNQ was dissolved in 650 ml boiling ethanol (0.05 M) then 10 g NMP-MS in 325 ml boiling ethanol (0.1 M) was added. The mixture was cooled to room temperature and then filtered, washed with ethanol. The dark solid was crystallized from 500 ml acetonitrile, washed with acetonitrile and dried at room temperature.

Electrode Surface Modification with NMP-TCNQ

NMP-TCNQ is insoluble in water. Pure NMP-TCNQ was dissolved in tetrahydrofuran and then coated on an electrode surface was not stable and gave a high background current. A stable surface coating was formed by forming a paste in tetrahydrofuran (THF) with 95% NMP-TCNQ and 5% by weight low molecular weight polyvinylchloride. A drop of the paste was coated on a dry carbon electrode surface and dried at room temperature. The formed black coating was stable and not readily removed by washing.

To a microcell with a NMP-TCNQ modified electrode was added 0.1ml Tris buffer with NADP and 0.35 units ICD. The background current was 5 nA at 0 V and the signal increased to 417 nA on addition of isocitrate. This showed that NMP-TCNQ coated electrodes were suitable for an ICD system without added soluble mediators.

EXAMPLE 6

This example illustrates the co-immobilization of ICD and a mediator on the electrode surface.

A glassy carbon electrode was first coated with NMP-TCNQ-PVC paste and dried. Then ICD-Au sol was evaporated onto the coating surface. Then Tris buffer with NADP was added and background current of 5 nA measured at 0 V. The signal increased to 231 nA on addition of isocitrate. This indicated that both ICD and mediator could be immobilized on the electrode surface.

EXAMPLE 7

This example illustrates co-immobilization of ICD, mediator and cofactor on an electrode surface.

NADP was added to the NMP-TCNQ-PVC paste before coating onto a glassy carbon electrode surface. ICD-Au sol was then evaporated onto the coating. The formed electrode contained the key elements for signal generation, except the substrate, isocitrate.

EXAMPLE 8

The following example illustrates a bioelectrode sensitive to low levels of mercury ion

Detection of Mercury Ion in Aqueous Solution

Figure 5:
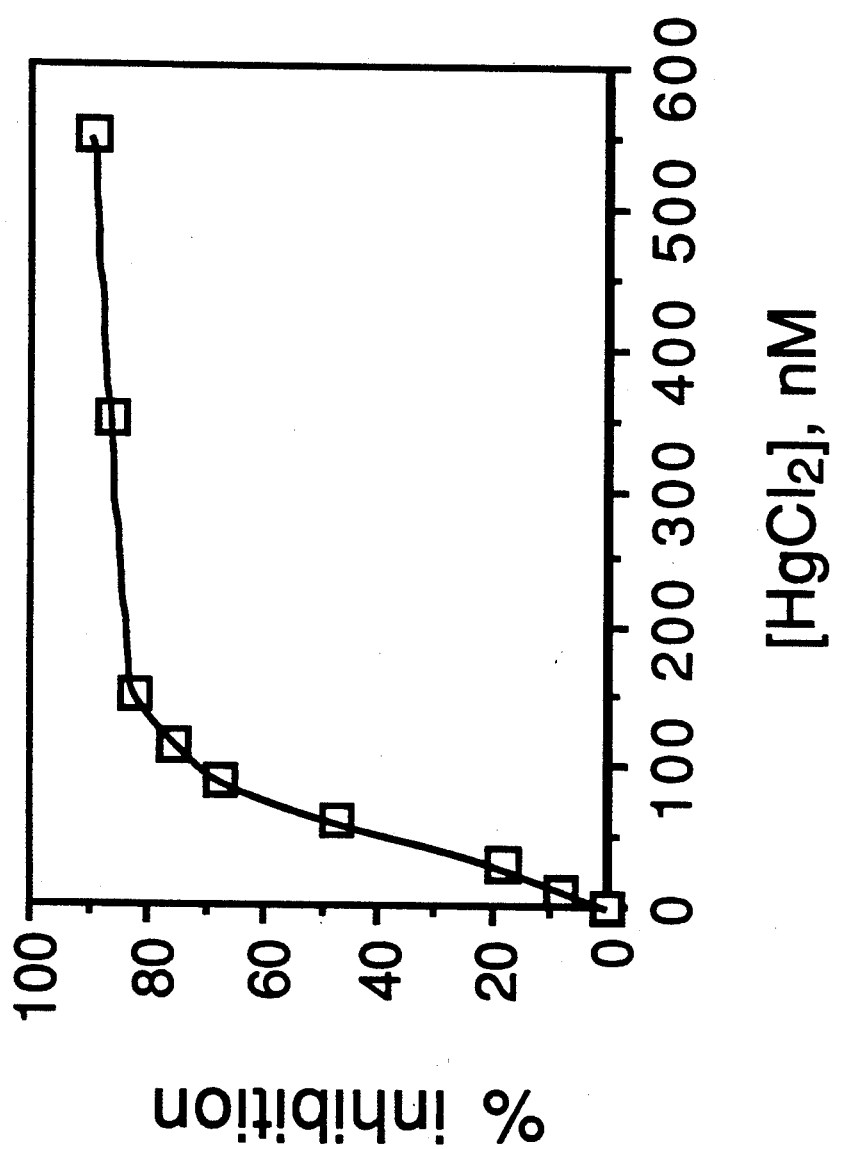
FIG. 5 is the amperometric response to mercury ion using a colloidal gold/ADH bioelectrode prepared by deposition on glassy carbon.
Figure 6:
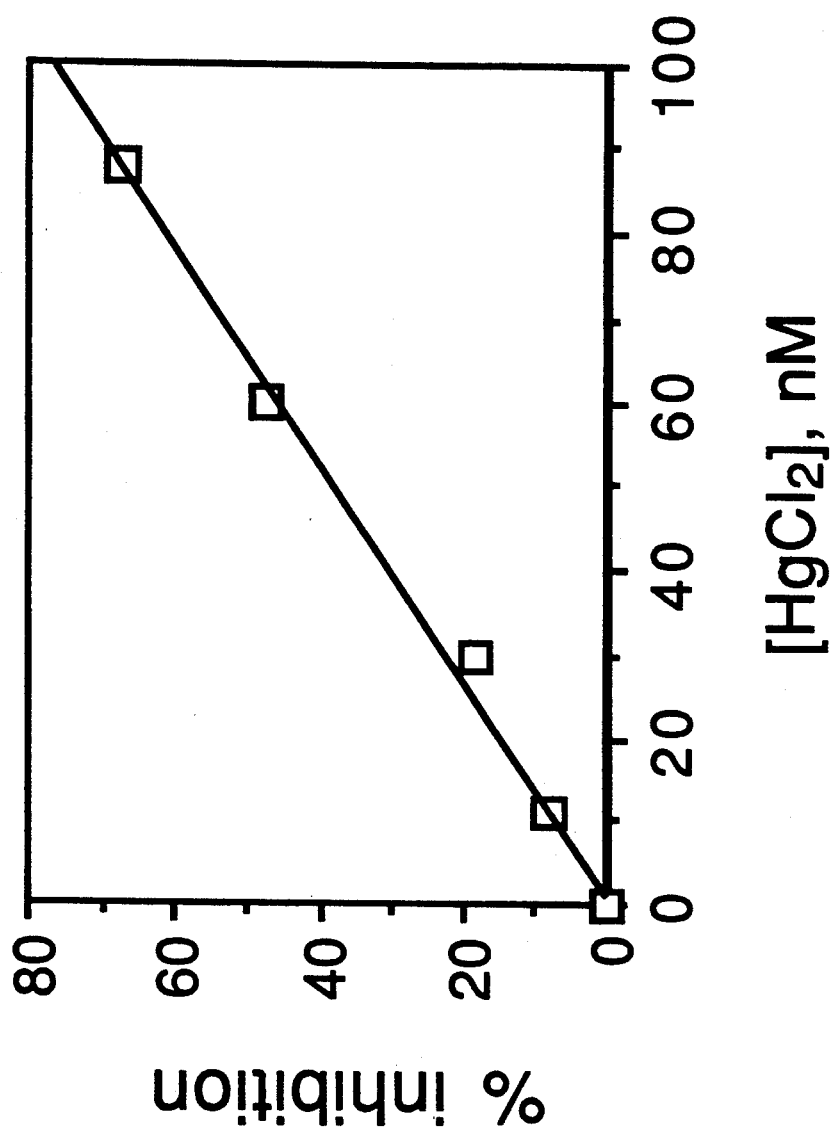
FIG. 6 illustrates the linear response of a glassy carbon bioelectrode prepared, from deposition of colloidal gold/ADH to mercury ion.

A bioelectrode was prepared from colloidal gold adsorbed alcohol dehydrogenase according the procedure of Example 2 for ICD. Measurements were made in the microcell as described in Example 1 using various concentrations of mercury. The calibration curve obtained is shown in FIG. 5. The linear portion of the curve is shown in FIG. 6, indicating a linear response in at nanomolar levels of mercury ion. The inhibition was irreversible and was specific for mercury in the presence of added lead ion.

EXAMPLE 9

The following example illustrates the general construction of a biosensor fabricated from a tri-electrode strip combined with an electronic analysis and display unit. The example is intended to illustrate one of many possible devices with commercial application.

Figure 7:
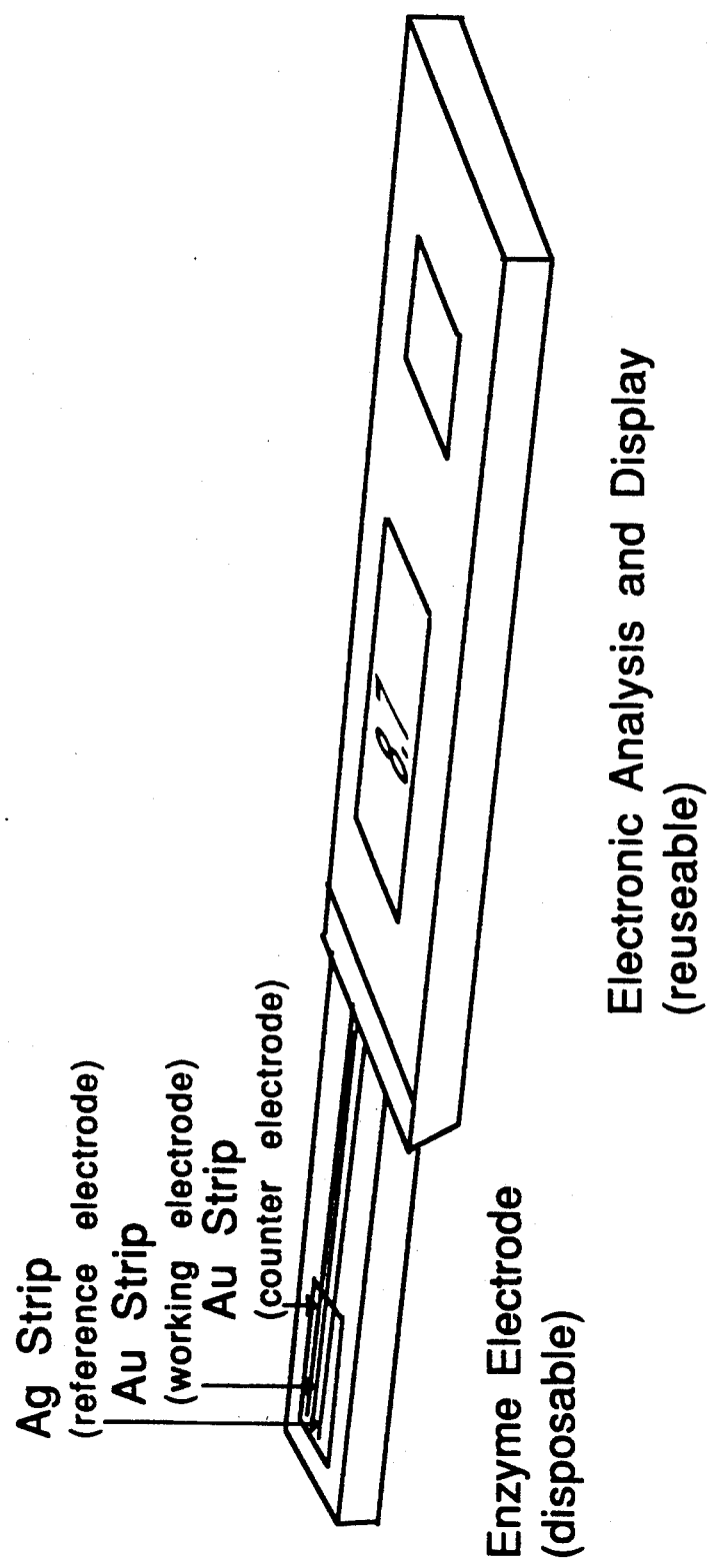
FIG. 7 is a schematic electrode configuration showing a construction with three microfabricated electrode strips. Reusable and disposable parts are indicated.

A disposable tri-electrode strip of the general design shown in FIG. 7, was fabricated from a glass plate with vapor-deposited gold The unmodified gold coating was divided into three isolated gold strips. Silver was selectively electrodeposited on one of the gold strips. Second enzyme was successfully immobilized on colloidal gold with retention of catalytic activity and then the colloidal gold-adsorbed enzyme prepared in accordance with Example 2 was selectively deposited on one of the two remaining gold strips. The third gold strip was left bare. In this embodiment, the silver coated channel acts as a reference electrode, the bare gold channel acts as a counter electrode, and the colloidal gold/enzyme coated channel acts as a working electrode The three-electrode strip responded to a standard enzyme substrate in a manner comparable to single channel enzyme sensors.

The tri-electrode strip will fit into the tip of a reusable electronic analysis and display unit, making an electrical connection with contacts on the inserted end of the strip. A small volume of sample is placed on the sensing end of the strip and catalytic current determined from a digital readout.

PROPHETIC EXAMPLE 10

The following examples illustrates a contemplated method for determination of lead ion in various materials where detection may be considered important Detection of Lead Ion in Urine A 10 µl urine sample is adjusted to a pH of about 8.5, then measured for lead ion as in Example 1.

Detection of Lead Ion in Wastewater

Measurement of lead in wastewater is conducted as in Example 1. Controls will determine if interfering metal ions are present (Sheikh and Townshend, 1974).

REFERENCES

The references listed below are incorporated herein by reference to the extent that they supplement, explain, provide a background for or teach methodology, techniques and/or compositions employed herein.

Albery, W.J., Cass, A.E.G., Mangold, B.P. and Shu, Z.X. *Biosensors & Bioelectronics* 5, 397 (1990).
Almestrand, L., Betti, M., Hua, C., Jagner, D. and Renman, L., *Anal. Chim. Acta* 209, 339-343 (1988).
Baum, P. and Czok, R., Biochem. Z. 332, 121 (1959).
Botre, C., Botre, F., Jommi, G. and Signorini, R., *J. Med. Chem.* 29, 1814 (1986).
*Chemical and Engineering News*, page 17, Oct. 14, 1991.
Fair, B.D. and Jamieson, A.M., *J. Colloid Interface Sci.* 77, 525 (1980).
Guilbault, G.G., Brignac, P., Jr., and Zimmer, M., *Anal. Chem.* 40, 190-196 (1968).
Guilbault, G.G., "*Enzymatic Methods of Analysis*", Pergamon Press, 1970.
Gunasingham, H., Delangin, R.R., Fleet, B., Narayanan, B. and Tang, T.F., *Instruments for Science*, Cole-Palmer Instrument Company, Chicago, IL, 1989).
Holleck, G.L., *J. Electrochem. Soc.* 119, 1158 (1972).
Kamata, S. and Onoyama, K., *Anal. Chem.* 63, 1295 (1991). Kratochvil, B., Boyer, S.L., and Hicks, G.P., *Anal. Chem.* 39, 45-51 (1967).
Linde, H.W., *anal. Chem.* 31, 2092 (1959).
Mealor, D., and Townshend, A., *Talanta* 15, 747 (1968).
Morrissey, B.W. and Han, C.C., *J. Colloid Interface Sci.* 65, 423 (1976).
Sheikh, R.A. and Townshend, A., *Talanta* 21, 401-409 (1974).
Smit, M.H. and Cass, A.E.G., *Anal. Chem.* 62, 2429-2436 (1990).
Toren, E.C. and Burger, F.J., *Mikrochimica Acta (wien)*, 5389-545 (1968).
Tran-Minh, C. Pandey, P.C. and Kumaran, S., *Biosensors & Bioelectronics* 5, 461 (1990).

What is claimed is:

1. A surface-modified bioelectrode for detecting nanomolar levels of lead or mercury ion consisting essentially of a colloidal gold adsorbed enzyme deposited onto an d in contact with a conducting surface to form a coating thickness of between about 4-12 monolayer a on said conducting surface wherein inhibition of the enzyme detectably affects current generated from redox reactions catalyzed by the enzyme when the surface modified bioelectrode is suitably coupled wit a reference electrode.

2. The biodelectrode of claim 1 wherein the enzyme comprises an oxidase or a dehydrogenase.

3. The bioelectrode of claim 1 wherein the enzyme comprises isocitrate dehydrogenase.

4. The bioelectrode of claim 1 wherein the enzyme comprises alcohol dehydrogenase.

5. The bioelectrode of claim 1 wherein the inhibition by lead or mercury ion is irreversible.

6. The bioelectrode of claim 1 further comprising a mediator.

7. The bioelectrode of claim 6 wherein he mediator comprises N-methylphenazine methosulfate, phenoxazine, ferrocene or N-methylphenazine.

8. The bioelectrode of claim 1 wherein the enzyme/colloidal gold is deposited on an electrode surface by evaporation.

9. The bioelectrode of claim 1 wherein the enzyme/colloidal gold is deposited on an electrode surface by electrodeposition.

10. The bioelectrode of claim 1 wherein the conducting surface is glassy carbon.

11. The biosensor of claim 1 further comprising dispersing the enzyme within a membranous or gelatinous film located on the bioelectrode surface.

12. The biosensor of claim 11 wherein the bioelectrode surface is gold, glassy carbon, colloidal gold or platinum.

13. The biosensor of claim 11 wherein a cofactor or mediator is included within the film.

14. A bioelectrode of the detection of lead ion concentrations of a least 10 µg/dl consisting essentially of colloidal gold adsorbed isocitrate dehydrogenase deposited to form a coating thickness of between about 4-12 nonlayers on a glassy carbon surface with AND or NADP.

15. The biodelectrode of claim 14 wherein the colloidal gold is between about 20 and 60 nm diameter.

16. The bioelectrode of claim 14 further comprising a mediator.

17. The bioelectrode of claim 16 wherein the mediator is N-methylphenazine methosulfate.

18. A biosensor comprising a reference electrode and a bioelectrode according to claim 1, said bioelectrode having a surface near or one which is located an enzyme capable of catalyzing a redox reaction wherein presence of lead or mercury ion concentrations less tan about 10 µg/dl adversely affects a current generated in the presence of a substrate.

19. The biosensor of claim 18 wherein he metal ion is lead.

20. The biosensor of claim 18 wherein the enzyme is isocitrate dehydrogenase.

21. The biosensor of claim 18 wherein he metal ion is mercury.

22. The biosensor of claim 18 wherine he enzyme is alcohol dehydrogenase.

23. An apparatus for detecting metal ion levels in fluids, comprising:
a receptacle having walls for containing a fluid sample;

a biosensor in accordance with claim 18 placed to allow contact with said fluid sample; and a detector positioned to receive a signal from the biosensor wherein the signal is obtained from current generated from a redox reaction catalyzed by the enzyme located on the bioelectrode surface.

24. The apparatus of claim 23 wherein the current generated is inversely related to an amount of metal ion present in the fluid sample.

25. The apparatus of claim 23 further comprising a counter electrode.

26. The apparatus of claim 23 further comprising an electronic analysis and display component.

27. The apparatus of claim 26 wherein the electronic analysis and display component is reusable.

28. The apparatus of claim 23 wherein the bioelectrode is disposable.

29. The apparatus of claim 23 wherein the metal ion detected is lead ion.

30. The apparatus of claim 23 wherein the metal ion detected is mercury ion.

* * * * *

UNITED STATES PATENT AND TRADEMARK OFFICE
CERTIFICATE OF CORRECTION

PATENT NO. : 5,217,594  Page 1 of 2

DATED : June 8, 1993

INVENTOR(S) : Henkens *et al.*

It is certified that error appears in the above-identified patent and that said Letters Patent is hereby corrected as shown below:

In column 15, line 15, delete "illustrates" and replace with --illustrate--.

In column 16, line 2, delete "an d" and replace with --and--.

In column 16, line 4, delete "layer a" and replace with --layers--.

In column 16, line 7, change "wit" to --with--.

In column 16, line 13, change "biodelectrode" to --bioelectrode--.

In column 16, line 19, change "he" to --the--.

In column 16, line 38, change the first "of" to --for--.

In column 16, line 42, change "AND" to --NAD--.

In column 16, line 52, change "one" to --on--.

In column 16, line 54, change "tan" to --than--.

In column 16, line 47, change "he" to --the--.

In column 16, line 61, change "he" to --the--.

UNITED STATES PATENT AND TRADEMARK OFFICE
CERTIFICATE OF CORRECTION

PATENT NO. : 5,217,594
DATED : June 8, 1993
INVENTOR(S) : Henkens et al.

It is certified that error appears in the above-indentified patent and that said Letters Patent is hereby corrected as shown below:

In column 16, line 63, delete "wherine he" and replace with --wherein the--.

Signed and Sealed this

Twenty-fifth Day of January, 1994

Attest:

BRUCE LEHMAN

*Attesting Officer*  *Commissioner of Patents and Trademarks*